(12) United States Patent
Tumlinson et al.

(10) Patent No.: US 10,045,692 B2
(45) Date of Patent: Aug. 14, 2018

(54) SELF-REFERENCED OPTICAL COHERENCE TOMOGRAPHY

(71) Applicant: Carl Zeiss Meditec, Inc., Dublin, CA (US)

(72) Inventors: Alexandre R. Tumlinson, San Leandro, CA (US); Paul F. Stetson, Piedmont, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 15/429,084

(22) Filed: Feb. 9, 2017

(65) Prior Publication Data

US 2017/0231488 A1     Aug. 17, 2017

Related U.S. Application Data

(60) Provisional application No. 62/294,020, filed on Feb. 11, 2016.

(51) Int. Cl.
*A61B 3/10* (2006.01)
*A61B 3/12* (2006.01)
*A61B 3/00* (2006.01)

(52) U.S. Cl.
CPC ........... *A61B 3/102* (2013.01); *A61B 3/0025* (2013.01); *A61B 3/0041* (2013.01); *A61B 3/1005* (2013.01); *A61B 3/12* (2013.01)

(58) Field of Classification Search
CPC ........... A61B 3/0008; A61B 3/14; A61B 3/12; A61B 3/102; A61B 3/0025
USPC .................................................. 351/200–246
See application file for complete search history.

(56) References Cited

U.S. PATENT DOCUMENTS

| | | | |
|---|---|---|---|
| 7,720,526 B1 * | 5/2010 | Modell | A61B 5/0066 356/407 |
| 9,332,902 B2 | 5/2016 | Tumlinson et al. | |
| 2006/0132710 A1 * | 6/2006 | Itoh | A61B 3/14 351/206 |

(Continued)

OTHER PUBLICATIONS

Choi et al., "Phase-Sensitive Swept-Source Optical Coherence Tomography Imaging of the Human Retina with a Vertical Cavity Surface-Emitting Laser Light Source", Optics Letters, vol. 38, No. 3, Feb. 1, 2013, pp. 338-340.

(Continued)

*Primary Examiner* — Mohammed Hasan
(74) *Attorney, Agent, or Firm* — Morrison & Foerster LLP (57) ABSTRACT

Systems and methods that use interference signal from a sample tissue (e.g. retina) obtained in a self-referenced manner to obtain one or more characteristics about the sample tissue, such as thickness and intensity information, are discussed in the present disclosure. One example method of analyzing the sample tissue using an interferometry system includes illuminating the sample tissue with a beam of light using a spectrally broadband source. Scattered light signal is collected from the sample tissue at a detector. The signal results from optical interference between light scattered from multiple scatterers located at different depths in the tissue. The light signal is dominated by light scattered from a scatterer located within the bulk of the tissue. One or more characteristics of the sample tissue are determined based on the collected signal.

15 Claims, 9 Drawing Sheets

(56) References Cited

U.S. PATENT DOCUMENTS

| | | | |
|---|---|---|---|
| 2006/0187462 A1* | 8/2006 | Srinivasan | A61B 3/102 356/479 |
| 2014/0221827 A1* | 8/2014 | Motaghiannezam | G01N 21/4795 600/425 |
| 2016/0209201 A1 | 7/2016 | Everett et al. | |
| 2017/0112374 A1 | 4/2017 | Hathaway et al. | |

OTHER PUBLICATIONS

Fingler et al., "Volumetric Microvascular Imaging of Human Retina Using Optical Coherence Tomography with a Novel Motion Contrast Technique", Optics Express, vol. 17, No. 24, Nov. 23, 2009, pp. 22190-22200.

Hofer et al., "Signal Post Processing in Frequency Domain OCT and OCM using a Filter Bank Approach", Proceedings of SPIE, The International Society for Optical Engineering, 2007, 6 pages.

Krstajić et al., "Tissue Surface as the Reference Arm in Fourier Domain Optical Coherence Tomography", Journal of Biomedical Optics, vol. 17, No. 7, Jul. 2012, pp. 071305-1-071305-6.

Ozcan et al., "Minimum-Phase-Function-Based Processing In Frequency-Domain Optical Coherence Tomography Systems", J. Opt. Soc. Am. A, vol. 23, No. 7, Jul. 2006, pp. 1669-1677.

Shechtman et al., "Phase Retrieval with Application to Optical Imaging", arXiv:1402.7350v1 [cs.IT], Feb. 2014, 25 pages.

Waldspurger et al., "Phase Recovery, Maxcut and Complex Semidefinite Programming", arXiv:1206.0102v3 [math.OC], Jul. 2013, 28 pages.

Wang et al., "A Practical Approach to Eliminate Autocorrelation Artefacts for Volume-Rate Spectral Domain Optical Coherence Tomography", Phys. Med. Biol., vol. 51, 2006, pp. 3231-3239.

Wojtkowski et al., "In Vivo Human Retinal Imaging by Fourier Domain Optical Coherence Tomography", Journal of Biomedical Optics, vol. 7, No. 3, Jul. 2002, pp. 457-463.

Yang et al., "Iterative Algorithms for Ptychographic Phase Retrieval", Technical report LBNL-4598E, 2011, 32 pages.

Yun et al., "Pulsed-Source and Swept-Source Spectral-Domain Optical Coherence Tomography with Reduced Motion Artifacts", Optics Express, vol. 12, No. 23, Nov. 15, 2004, pp. 5614-5624.

\* cited by examiner

FIG. 1 (Prior-art)

SELF-REFERENCED OPTICAL COHERENCE TOMOGRAPHY

PRIORITY

The present application claims priority to U.S. Provisional Application Ser. No. 62/294,020 filed Feb. 11, 2016, the contents of which are hereby incorporated by reference.

TECHNICAL FIELD

The present application relates to the field of interferometric imaging. In particular, the application relates to the collection and analysis of interferometric systems in which the interferometric signal is the result of interference between the inherent scattering of scatterers located within a tissue.

BACKGROUND

Optical coherence tomography (OCT) is a noninvasive, noncontact imaging modality that uses coherence gating to obtain high-resolution cross-sectional images of tissue microstructure. Several implementations of OCT have been developed. In frequency domain OCT (FD-OCT), the interferometric signal between light from a reference and the back-scattered light from a sample point is recorded in the frequency domain typically either by using a dispersive spectrometer in the detection arm in the case of spectral-domain OCT (SD-OCT) or rapidly tuning a swept laser source in the case of swept-source OCT (SS-OCT). After a wavelength calibration, a one-dimensional Fourier transform is taken to obtain an A-line spatial distribution of the object's scattering profile.

OCT provides high contrast 3D visualization of moderately scattering materials using interference of light scattered from a sample (e.g., human eye), with light from a reference surface. Retinal imaging is the most highly developed application for OCT. Thickness information about the retina is highly valuable in the diagnosis of diabetic macular edema (DME), early age-related macular degeneration (AMD), and central serous retinopathy (CSR) among other conditions.

OCT is however expensive. OCT devices are typically complicated instruments including a sample arm with x/y scanner, and an adjustable length reference arm. Very high source brightness is required because is its highly advantageous to have a single spatial mode illuminator, and illumination time is limited by phase washout due to relative motion of the in vivo sample and the reference arm of the system. High spectral resolution is required to achieve a large imaging depth range.

From the inception of FD-OCT, it has been observed that a signal can be decomposed into a portion resulting from the light scattering from the tissue interfering with a dominant reference light and a portion resulting from interfering the light scattering from the tissue interfering with itself. The portion of the signal from sample light interfering with itself has almost uniformly been considered an undesirable image artifact, usually called 'autocorrelation noise. Various techniques have been adapted over the years to suppress the autocorrelation artifact. The first published account of frequency domain images of the human retina includes a description of a method to modulate the length of the reference arm to attenuate the autocorrelation portion of the signal (Wojtkowski, M., et al. 2002 "In vivo human retinal imaging by Fourier domain optical coherence tomography." *Journal of Biomedical Optics* 7 (3): 457-463). The method most commonly used in commercial spectral domain OCT (SD-OCT) systems imaging the eye today use a strong reference power such that any autocorrelation noise is weak relative to the shot noise of the system. Alternatively, in swept source systems, the use of dual balanced detection blocks signal which is common mode, including the autocorrelation artifact.

'Common path' OCT systems simplified the OCT beam-path to a Fizeau interferometer, such that an optical window in the beam path or even the tissue surface itself could act as the reference surface for interferometric imaging. The important factor for clean imaging was that the reference surface should be dominantly bright such that the autocorrelation of the reflectance profile could be approximated as a correlation of the reflectance profile with a delta function, and thus maintain a very good representation of the reflectance profile of the tissue. In the case where the tissue surface could act as the reference surface, the Fresnel reflection from the air-water interface could be strong enough if the angle of reflection could be captured by the system. In order to supplement this intrinsic reflection, a method was devised to enhance the surface reflection by applying a highly reflective powder to the proximal surface of the organ to be imaged. Such self-referenced systems have cost advantages in terms of system simplicity and have a stability advantage because the systems are relatively insensitive to motion in the axial direction of the sample relative to the imaging system. An obvious drawback, but potential advantage of such tissue surface referenced images is that information about the geometry of the surface is discarded prior to measurement. The image of the tissue is flattened to the reference surface automatically. If the surface geometry does not contain useful information, this flattening makes the signal easier to measure because it contains lower frequency spectral modulations, may make visualization and analysis of the signal easier if the primary interesting information is the tissue thickness from the surface, and finally makes the total image size smaller.

Figure 1:
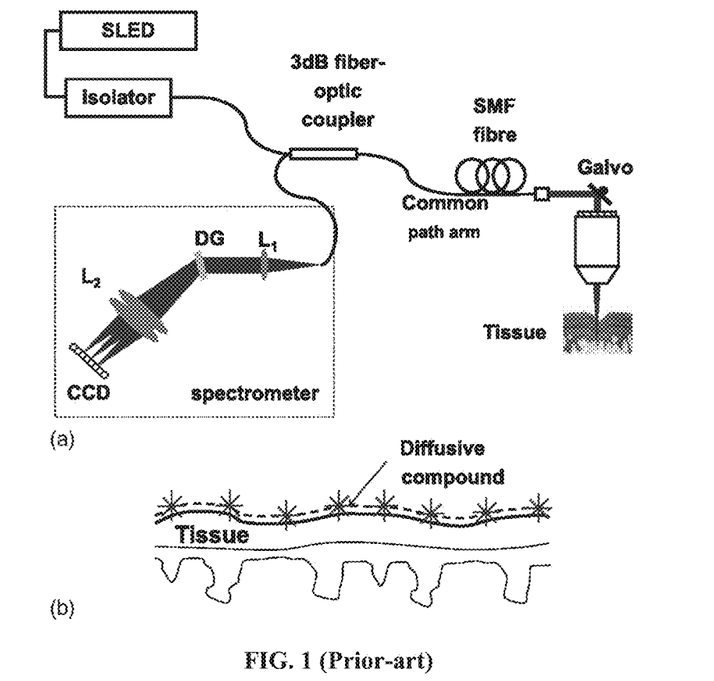
FIG. 1 illustrates an example prior-art Fourier domain OCT system without a reference arm.

FIG. 1(a) illustrates an example prior-art Fourier domain OCT system without a reference arm (Krstajić, N., Brown, C. T. A., Dholakia, K., and Giardini, M. E. (2012) "Tissue surface as the reference arm in Fourier domain optical coherence tomography." J. Biomed. Opt 17, 071305-071305). As depicted, a super luminescent diode (SLED) illuminates the tissue via a 3-dB fiber coupler and microscope objective with a working distance of 25 mm and lateral resolution of 17 μm. The reference arm shares the physical path of the sample arm, and is generated by the diffuse surface on the top of the tissue (see FIG. 1(b)). Due to its common path configuration, the single mode fiber (SMF) used can be of arbitrary length. Backscattered spectra from the common arm are detected by a custom transmissive spectrograph containing dispersive optics (diffraction grating (DG) and lenses $L_1$ and $L_2$) and a line CCD detector. Either specular reflection from the air tissue interface or an extrinsic scattering compound is applied to increase reflection and create a dominant peak for correlation existing entirely on the proximal side of the tissue of interest.

It would be acceptable for many applications of retinal OCT to maintain information only about the thickness of tissue layers, and discard information about the tissue surface, such as the curvature of the retina. In fact, most OCT systems do not record the beam pivot geometry with sufficient accuracy to provide good information about the shape of the sphere of the eye, and many analyses of retinal OCT data first flatten the data to simplify or constrain the segmentation process. Maintaining the reference arm to a closely matched pathlength and identical polarization state to the sample arm adds challenges that would be preferably avoided in a low cost OCT system. On the other hand, very few locations on the human retina produce a specular reflection which is directed back towards the pupil and can be used a reference surface for a potential reference arm. Likewise external application of a highly scattering agent across the retinal surface would be unacceptable.

SUMMARY

Here we describe a method that uses interference signal from the retina that can be obtained in a self-referenced manner to obtain useful characteristics about a sample tissue (e.g., retina) such as thickness and intensity information, despite the fact that no surface exists which can properly be called the reference surface. Devices are also described which are optimized to measure this signal. Finally several methods of using the signal for diagnostic purposes are described.

One embodiment of the present application is a method of analyzing a sample tissue using an interferometry system comprising: illuminating the sample tissue with a beam of light using a spectrally broadband source; collecting light signal scattered from the sample tissue at a detector, said signal resulting from optical interference between light scattered from multiple scatterers located at different depths in the sample tissue, wherein the light signal is dominated by light scattered from a scatterer located within the bulk of the sample tissue; determining one or more characteristics of the sample tissue based on the collected signal, said characteristics containing information about the distribution of depth separation between the multiple scatterers within the tissue; and displaying or storing the characteristics or a further analysis thereof.

The signal acquired from the self-referenced interferometry device discussed in the present application is dominated by the autocorrelation of the tissue reflectance spectrum, which provides information about the separation between multiple scatterers located at different depths in the tissue. The device does not contain a defined length path that acts as the reference for the depth measurement, so the acquired data is free of information about the absolute distance of a scatterer from a plane in the instrument. From this autocorrelation signal, the device may extract signals reflecting characteristics containing information about the distribution of depth separation between the multiple scatterers within the tissue. Some of the characteristics may include, for example, total reflectance of the tissue and the thickness of tissue elements. The device may output or display, for example and without limitation, 1) auto correlation 'B-scans' which allows the viewer to make judgments about the depth of structures in the retina, 2) enface maps of the total reflectance, 3) enface maps of retinal thickness, 4) superimposed maps of thickness overlaid on total reflectance, 5) maps of change(s) from a previous state, 6) maps indicating contrast of stable tissue vs. tissue with inherent motion due to blood flow, 7) indication that threshold of thickness or change has been surpassed, and 8) best estimation of true retinal structure 'B-scans' algorithmically recovered from autocorrelation signal and additional prior information, or multiple acquisitions.

A preferred embodiment of the invention includes line-field illumination and detection (either swept source, spectral domain, or hybrid), a simple single axis scanner to achieve an area scan, and a split pupil configuration where the light illuminating the retina is passed through a different portion of the pupil of the eye than light returning from the retina.

Compared to prior-art 'self-referenced OCT' (as discussed in the background section)—which used either a very bright specular reflection at an air-tissue interface, or an artificial highly scattering agent applied at the surface of a tissue to achieve true depth resolved imaging, the systems and methods presented in the present disclosure depend on the inherent scattering of scatterers located at different depths within a tissue and can report the distance between those scatterers to provide an impression of total tissue layer thickness. Useful reporting of retina thickness and approximate 'imaging' of the retina is aided by the retinal pigment epithelium (RPE) which forms the dominant scatterer in a single bright layer buried underneath the retina within the bulk of the retina. A problem of confusing signal from light scattered by tissue deep to the RPE is solved by using a shorter wavelength than is traditionally used in ophthalmic OCT, thus enhancing the absorption of light by the RPE. The ambiguity of light coming from tissue deep to the RPE is further addressed by using the phase disruption caused by blood motion in the choriocapilaris, and optimizing the illumination and acquisition time to increase contrast to distinguish signal that arises above and below this layer.

Combination of self-referencing with line field enables long integration time that allows 1) safe power levels at low cost and 2) suppression of confusing sub RPE signal by phase washout, and further enables multimode sources at low cost.

Split aperture minimizes measurement of self-interference of components including anterior eye and imaging optics. Reconstruction approaches with constraints applied in spatial and frequency domain to optimize reconstruction of self-referenced signal.

It should be noted that the language used in the specification has been principally selected for readability and instructional purposes and not to limit the scope of the inventive subject matter.

BRIEF DESCRIPTION OF THE DRAWINGS

FIGS. 2A and 2B depict two different views of an exemplary self-referenced line field system according to one aspect of the present invention. In particular.

FIGS. 6A-E show simulated data from a single high density volume recorded from one human eye. In particular.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Autocorrelation signal (i.e., a portion of the signal from sample light interfering with itself) can be acquired from a traditional point scanning, frequency domain OCT system, with its reference arm blocked. From this autocorrelation signal, a device may extract signals reflecting characteristics of a sample tissue. Some characteristics may include, for example and without limitation, the total reflectance of the tissue, the thickness of tissue elements, presence or absence of local blood flow, observable change relative to a previous measurement, measurement of tissue thickness relative to limits established in a normal population, etc. Many characteristics of tissue that are traditionally probed with OCT including a reference arm and reported for diagnostic purposes can also be probed with the currently described implementation of OCT without a reference arm such as ones discussed in reference to FIGS. 2A-B.

The amount of light scattered from the eye is the same as in the traditional OCT case, so in the shot noise limited case, there is sufficient light to create an interferogram with high sensitivity to small reflections. Typically, a modern point scanning OCT system depends on interferometric amplification of the sample light by the reference light to achieve close to shot noise detection. Therefore, either the power of the source should be dramatically increased, the integration time of its detector increased, or the noise in the detector significantly decreased such that the number of photons incident on each detector element is significant compared to the number noise electrons generated. The amount of light entering the eye can be only be increased to the safety and legal limits. Traditional OCT exposure times are limited by the axial motion of the eye relative to the external reference. Movement by one quarter of the wavelength of light during the time that wavelength is measured on the detector is sufficient to cause a complete reversal of interference phase and cancel any signal integrated during the exposure time (known as phase washout). Self-referenced OCT is much more tolerant to axial motion of the sample because there is not an external reference to move relative to. Exposure time is then limited again by the safe speed of at which a scanning laser of a given power may traverse the retina, or the lateral motion of the eye by a significant fraction of a speckle diameter—approximately the lateral dimension of an Airy disk given the numerical aperture of the light collection optics, as measured in the optical space of the retina. This potentially allows an increase of maximum exposure time in SD-OCT of about 100 us up to about 10 ms (assuming isotropic 2 mm/s motion, 840 nm center wavelength, and Airy disk diameter 20 um).

This 100× increase in exposure time can be prohibitively slow, and potentially unsafe if using a point scanning OCT system of the same power. An OCT system measuring multiple points or fields simultaneously, on the other hand, can maintain short total imaging time while increasing the exposure time per point on the tissue. The system can also illuminate with a greater total power distributed over a wide region. Such a 'parallel' OCT system may illuminate and measure from a continuous array of points, in a line or small area, or may sample spatially separated points. In the present application, we focus on line field systems, however other sampling methods are referenced and could also be used. Systems applicable to self-referenced retinal OCT closely resemble traditional retinal OCT systems with the omission of the reference arm. In one embodiment of the present application, field illumination is provided by either a spatially single mode or multimode source. In contrast to traditional OCT with a reference arm, precise alignment between sample and reference arms is not challenging, because the interference occurs completely within the sample tissue—inherently aligned with itself. The light may be provided by a superluminescent diode (SLD), tuned laser diode source, or incoherent array sources. LEDs may soon achieve the brightness required. Arrays of electrically pumped tunable vertical cavity surface emitting laser (VCSEL) sources are particularly attractive for this application.

Figure 2A:
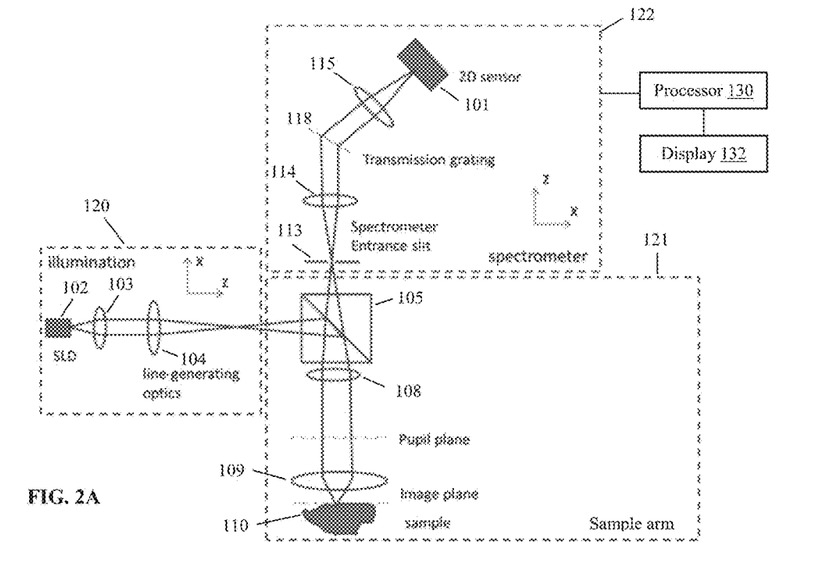
FIG. 2A shows a view with the x direction in the plane of the page.
Figure 2B:
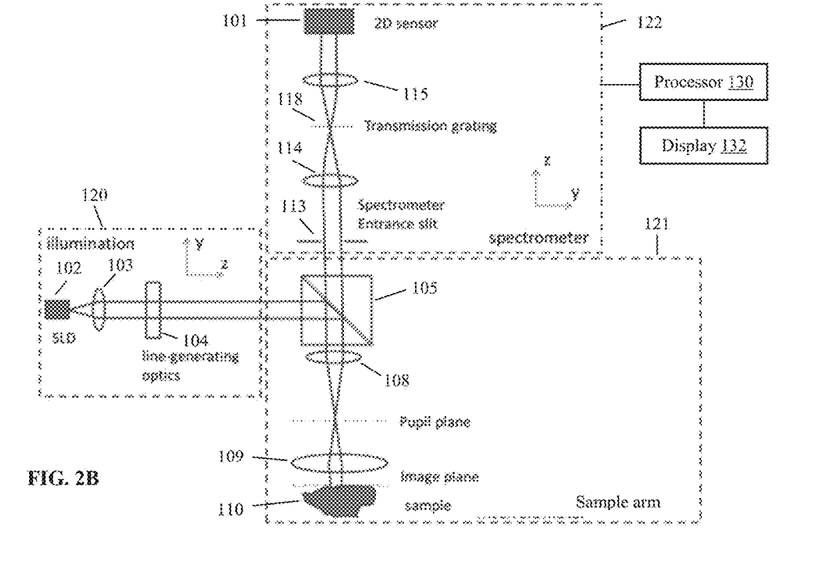
FIG. 2B shows a view where the illumination and the spectrometer have been rotated by 90 degrees compared to FIG. 2A (i.e., with the y direction in the plane of the page).

FIGS. 2A and 2B depict two different views of an exemplary self-referenced line field system capable of performing the methods of the present application. This line field system is much like previously described line field systems for the human eye (see for example, U.S. Pat. No. 9,332,902), but without a reference arm adjusted to be substantially the same length as the sample arm, and the exposure time of the system is greatly increased.

The illustration shown in each of FIGS. 2A and 2B is broken into three sections or blocks, illumination block 120, sample arm block 121, and detection block 122. The detection block 122 includes collection optics 114 and 115, a spectrometer having an entrance slit 113, a dispersion element 118, and a two-dimensional sensor array 101. As mentioned earlier, two different views of the self-referenced line field system are shown in FIGS. 2A and 2B. In particular, FIG. 2A shows a view with the x direction in the plane of the page. The beam path shown indicates the profile of the beam in the indicated axis. Where the profile narrows to a point, the beam is at an image plane relative to the sample plane in the indicated axis. In order to illustrate the layout of the orthogonal direction, FIG. 2B shows a view where the illumination and the spectrometer have been rotated by 90 degrees compared to FIG. 2A., i.e. with the y direction in the plane of the page. This view enables the visualization of the light path in the orthogonal direction as well. The beam path shown indicates the profile of a beam from a single direction, corresponding to the optical axis. Where the profile narrows to a point, the beam is at a Fourier plane relative to the sample plane in the indicated axis. The self-referenced line field system will now be described in further detail in reference to the figure.

Broadband light 102 passes through a collimating lens 103 and through optics 104 to generate a line shaped focus in a beam. An SLD would be a typical light source, but any broadband light source could be used in the present invention and the line shape could be a property of the source instead of requiring additional optical elements. The source could also be swept in optical frequency. The line of light has extent in the y or vertical direction for this embodiment. The line of light is split at beam splitter 105. Light in the sample arm 121 passes through spherical lens 108, which collimates the light in the x-dimension and focuses the line of light in the y-dimension to have a beam waist at the pupil plane. After passing the pupil plane, the light in the sample arm is focused to a line on the sample 110 using one or more lenses 109. In the case of imaging the eye, focusing could be achieved all or in part using optical properties of the anterior segment of the eye itself. Light reflected from the sample 110 is directed towards the spectrometer entrance slit 113. The entrance slit 113 is elongated in the y dimension as illustrated in FIGS. 2A and 2B. The dispersive element within the spectrometer, in this case a transmission grating 118, disperses the light in the x-dimension, perpendicular to the elongated axis. The narrow axis of the spectrometer entrance slit 113 is imaged back into the space of the scattering object and is substantially overlapping with the line focus of the illumination, acting as a confocal gate or confocal selecting mechanism in one dimension. The spectrometer contains a two-dimensional sensor array 101 for measuring the light coming from the signal light path and generating a signal thereto. The signal results from optical interference between light scattered from multiple scatterers located at different depths in the sample 110. The signal is dominated by light scattered from a scatterer located within the bulk of the sample, such as the RPE. A processor 130 is operably connected to the spectrometer 122 for processing and determining one or more characteristics about the sample 110 based on the signal. The characteristics contain information about the distribution of depth separation between the multiple scatterers within the sample. The characteristics can be stored in the processor 130 or other storage medium or displayed on display 132. The processing and storing functions may be localized within the system or functions may be performed on an external processing unit to which the collected data is transferred. The processor could be dedicated to data processing or perform other tasks which are quite general and not dedicated to the system discussed herein. The processor 130 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion. The processor 130 can be part of the imaging device or be a stand-alone processor connected via cable or over the internet to the imaging device.

For a system including an instantaneously broadband source such as an SLD (shown by reference numeral 102), the detector 122 may resolve the spectrum by dispersing the light as a grating spectrometer. If the light source produces a changing optical frequency with time, a fast detector may resolve the spectrum in a serial manner. Hybrid systems may be advantageous where a swept laser is recorded on a spectrally dispersive sensor.

The beamsplitter 105 illustrated in FIGS. 2A and 2B has a transmission from the source to the eye α, and a reciprocal transmission from the eye to the detection of (1−α). It is possible to avoid these reciprocal losses of a partially reflective beamsplitter by introducing spatial beamsplitting at a pupil plane. It is typical for OCT systems to detect from a pupil significantly smaller than the aperture of the human eye. Using a smaller aperture typically results in loss of light, but helps maintain a large depth of focus and tolerance to pupil aberrations. Here we propose two different methods to spatially split the pupil with different resulting system effects (discussed with respect to FIGS. 3A-C and 4A-B, respectively). Splitting the pupil is also advantageous to suppress detectable back reflections from the optical system and the anterior of the eye.

Figure 3A:
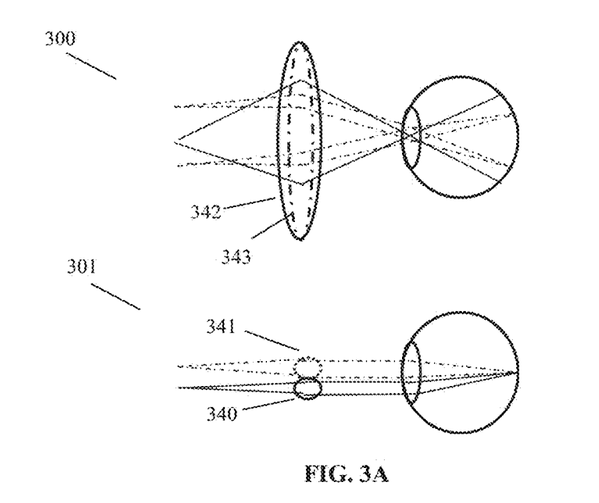
FIG. 3A shows an illustration of pupil split axis being parallel to line projection.
Figure 3B:
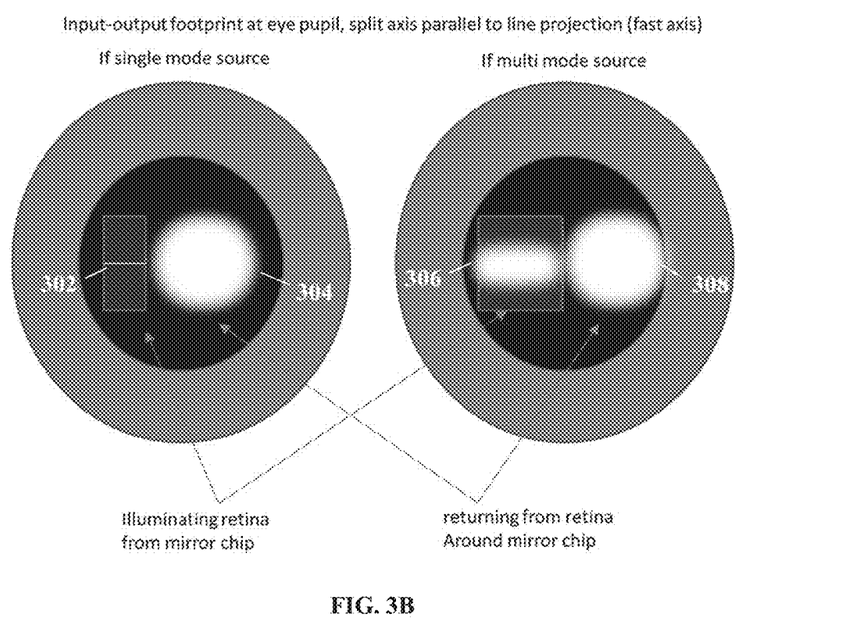
FIG. 3B shows input-output footprint at eye pupil, when the slit axis is parallel to the line projection.

FIG. 3A shows an illustration of the pupil split axis being parallel to line projection. Here, reference numerals 300 and 301 represent the top and side views of said illustration, respectively. Solid lines represent rays from the source to the retina. Dashed lines represent rays scattered from the retina towards the detector. Ovals representing optical elements near the eye (indicated by reference numerals 342 and 343) are separate for input 340 and output 341 paths. FIG. 3B shows the input-output footprint of the light at the eye pupil, when the slit axis is parallel to the line projection. The left image shows the case of a single mode source and the right image shows the case of a multi-mode source. In particular, reference numerals 302 and 304 represent the input (i.e., light illuminating retina) and output (i.e., light returning from retina) footprints, respectively, when a single mode source is used. Reference numerals 306 and 308 represent the input and output footprints, respectively, when a multi-mode source is used. The optical system is potentially very simple, however a small amount of defocus results in loss in intensity over the entire line, because the imaged line shifts away from the line of the detector. The system also requires a relatively large footprint on the pupil of the eye.

Figure 3C:
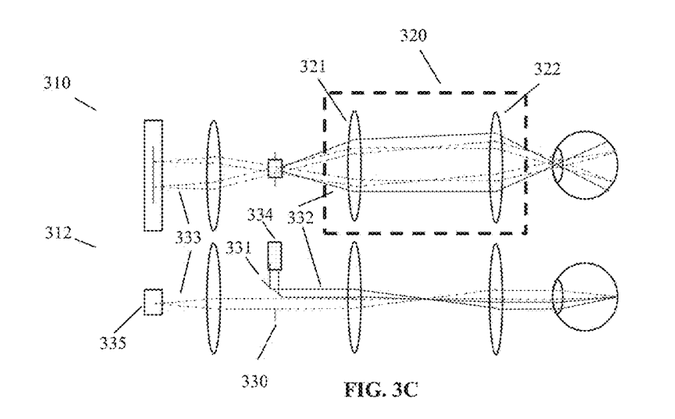
FIG. 3C shows an alternative illustration of FIG. 3A with a Badal optometer to achieve refractive correction.

FIG. 3C shows an alternative illustration of the pupil split axis being parallel to line projection including a Badal optometer 320 to achieve refractive correction. Here, reference numerals 310 and 312 represent the top and side views of said alternative illustration, respectively. Optics 321 and 322 near the eye are common for input path 332 and output path 333 and the beams are separated by a beam splitting element 331 at a relayed image of the pupil 330. Input paths originate at a source 334 and output paths terminate at a detector 335. Refractive correction is implemented by adjusting the distance between elements 321 and 322.

Figure 4A:
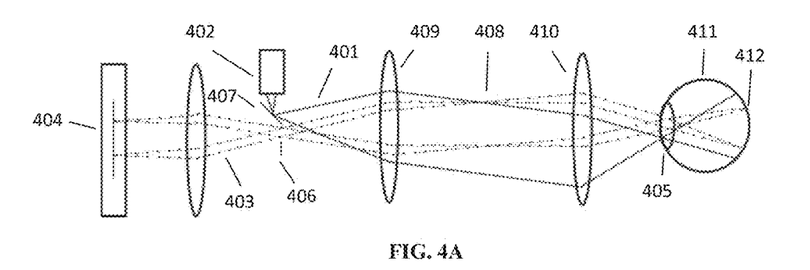
FIG. 4A shows an illustration of pupil split axis being perpendicular to line projection.
Figure 4B:
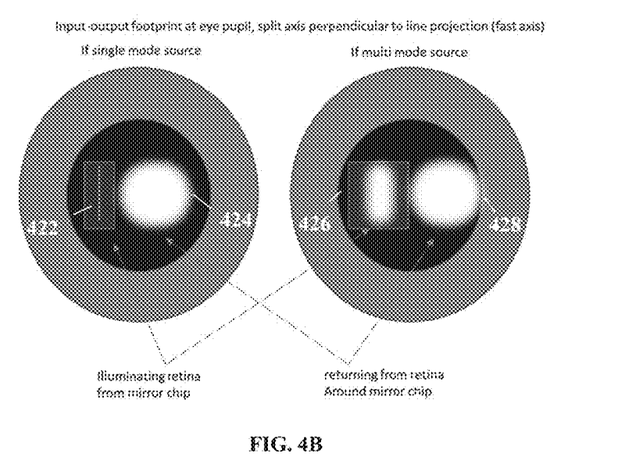
FIG. 4B shows input-output footprint at eye pupil, when the slit axis is perpendicular to the line projection.

FIG. 4A shows an illustration of a pupil split axis being perpendicular to the line projection. Light is introduced to the retina 412 on a source path 401 from a source 402, and returned from the retina 412 on a return path 403 towards a detector 404. The source path 401 and the return path 403 are spatially separated at the pupil 405 of the eye 411. The source path and the return path are again spatially separated at an image conjugate 406 of the eye pupil (pupil conjugate) along the optical path of the system. In such a pupil conjugate, a beam splitting optic 407 is placed to separate the source path from the return path. An intermediate image plane 408, conjugate to the retina, is shown between focusing optics 409 and 410 which may be adjusted to accommodate for refractive error of the eye. FIG. 4B shows the input-output footprint at the eye pupil, when the slit axis is perpendicular to the line projection. Similar to FIG. 3B, the left image illustrates the case for a single mode source while the right image shows the footprint for a multi-mode source. In particular, reference numerals 422 and 424 represent the input and output footprints, respectively, when a single mode source is used. Reference numerals 426 and 428 represent the input and output footprints, respectively, when a multimode source is used. Because the system causes an overlap of beams at all planes other than the pupil, the optical system must include a relay in order to separate the beams. The system is more complicated, however, because the defocus causes the imaged line to translate along the line of the detector, causing a shift in the image rather than a loss of detection.

Figure 5:
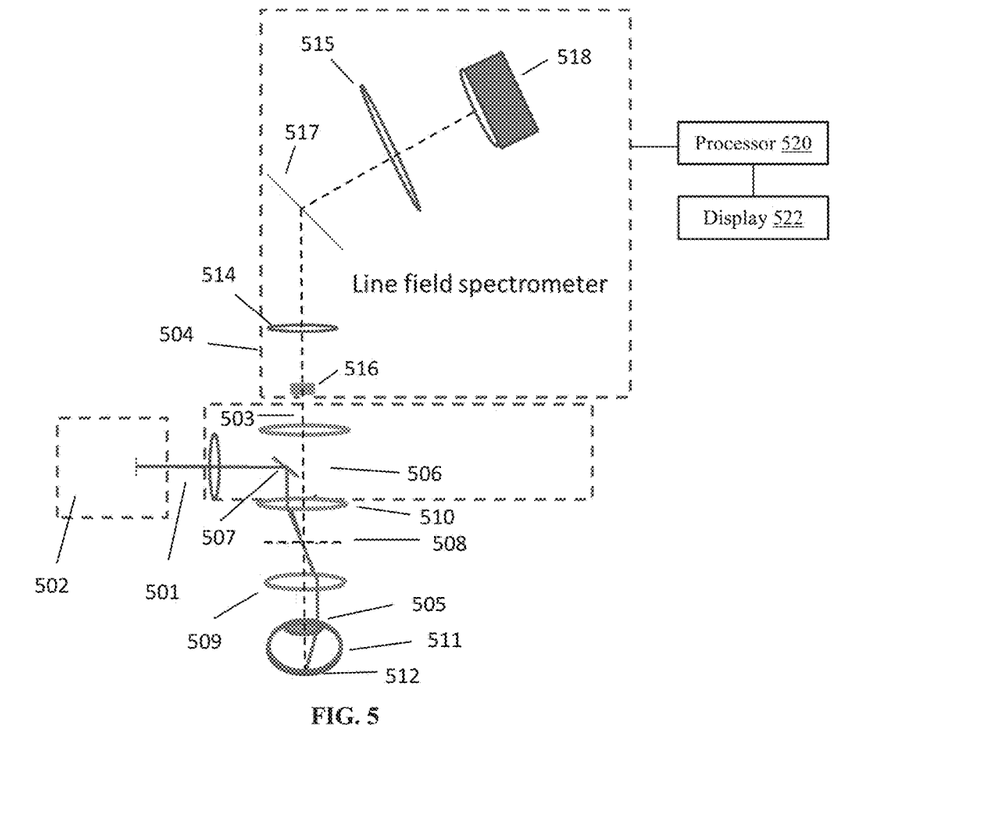
FIG. 5 is an example illustration of a system including pupil split.

FIG. 5 is an example illustration of a system including a pupil split. Light is introduced to the retina 512 on a source path 501 from a source 502, and returned from the retina on a return path 503 towards a detector 504. The output from the detector 504 is supplied to a processor 520 for processing and reconstructing data for image generation. The results can be stored in the processor 520 or other storage medium or displayed on display 522. The detector block 504, similar to the detector block in FIG. 2A, includes optics 514 and 515, a spectrometer having an entrance slit 516, a dispersion element 517, and a two-dimensional sensory array 518. The source path 501 and the return path 503 are spatially separated at the pupil 505 of the eye 511. The source path and the return path are again spatially separated at an image conjugate 506 of the eye pupil (pupil conjugate) along the optical path of the system. In such a pupil conjugate, a beam splitting optic 507 is placed to separate the source path 501 from the return path 503. An intermediate image plane 508 conjugate to the retina 512 is shown between focusing optics 509 and 510 which may be adjusted to accommodate for refractive error of the eye. An additional axis of scanning may be added to the system described as is well understood by those skilled in the art. For example, a scanning galvo mirror may be introduced at a pupil of the system. It may be advantageous to introduce additional optical elements to the system to create an additional pupil plane in which to place an angularly scanning mirror. An alternative means to scan a system includes introducing a translation at an image plane. This may be performed by shifting portions of the optical system or by a system of translating mirrors.

Axial separation between any two scatters in the posterior eye tissue is encoded in the frequency of modulation across the measured interference spectrum at any illuminated point on the fundus. Spectrally resolved detection may be performed by swept source or spectral domain systems. Measurements are spectrally resolved with sufficient density to resolve the tissue depth. Because only the tissue thickness must be resolved, and not departures of tissue from a fixed reference, this thickness and therefore resolution is less than required in a typical retinal OCT system.

The system should sample the lateral speckle field such that variations in speckle do not reduce interference contrast. If the detector elements are located in an image plane conjugate to the retina, the size of the detector elements should not be larger than a typical speckle. It is not necessary that the speckle field is sampled continuously, although this may be advantageous.

Spectral data from the system may be reconstructed in a processor to a spatially representative B-scan, analogous to the B-scan of traditional OCT, by a simple Fourier transformation across the variable k (propagation constant) at each lateral location across the retina. Data from the sampled spectrum may contain spectral distortions and need to be resampled first to be uniform in k as is well known in the art. Alternatively, discrete Fourier transforms or generalized filter banks may be used to produce a reconstruction (see for example, Hofer, B., Považay, B., Hermann, B., Unterhuber, A., Matz, G., Hlawatsch, F., and Drexler, W. (2007). "Signal post processing in frequency domain OCT and OCM using a filter bank approach." p. 64430O-64430O-6). Alternative reconstructions are possible as will be discussed later in this disclosure.

Although the image quality is generally inferior to that produced by traditional OCT with a reference arm, the tomograms produced by such a reconstruction can be manipulated in many similar ways to state-of-the-art tomograms. For example, the sum across the depth axis can be used to accurately describe the total reflectivity of the tissue and when performed across the area of the fundus can produce an image qualitatively equivalent to the 'OCT Fundus Images' available in commercial traditional OCT instruments. The reflectivity profile observed in the autocorrelation B-scan describes the axial distribution of thicknesses between scatters more than the exact location of a particular scatterer, however it can still be segmented for boundary conditions and characterized to estimate the total thickness of retinal tissue. If the data is acquired multiple times in sequence, the data can be compared to show differences. On a very short time scale, differences can highlight the localized presence of blood flow to create high resolution angiography maps. On a longer time scale, comparison between two time points can identify structural changes associated with disease progression. As can be illustrated by simulation, autocorrelation b-scans from relatively healthy eyes with an intact RPE appear qualitatively similar to traditional b-scans, flattened to the RPE surface which forms the dominant reflector in the interferometer. In such a case, the measurements derived by traditional segmentation may be well compared against limits established by measuring known normal individuals. It may even be possible to report estimates of specific tissue layer thickness such as retinal nerve fiber layer in such individuals. Such a comparison against normative limits may be specifically relevant to disease screening applications in populations without obvious eye disease, outside the traditional retina specialist practice. In eyes where the RPE is more significantly disrupted, where eye disease is already advanced, the diagnostic concern is very frequent to monitor for changes. Any change from baseline condition over a given threshold may constitute a characteristic which could trigger a more traditional office exam and possible treatment. Such an application in diseased eyes would be particularly advantageous for home monitoring for conversion from dry to wet age related macular degeneration, or monitoring for a specific edema or bleeding event related to monitoring known diabetic retinopathy.

To illustrate the utility of the data output of such a system (discussed above), data presented here is simulated from images of human eyes acquired from a traditional OCT instrument with a reference arm. The autocorrelation signal is simulated as mean(log 10(xcorr(R_z)), where 'R_z' represents the reflectivity profile of a tissue B-scan back-calculated from the recorded tomogram., 'xcorr' represents the autocorrelation function as numerically implemented in MATLAB software, 'log 10' represents the base 10 logarithm and is important primarily for display purposes to reduce the required output dynamic range, and 'mean' represents the mean of 5 B-scans, recorded at the same location. Because the autocorrelation function is symmetric, a one sided output is displayed as a B-scan.

Figure 6A:
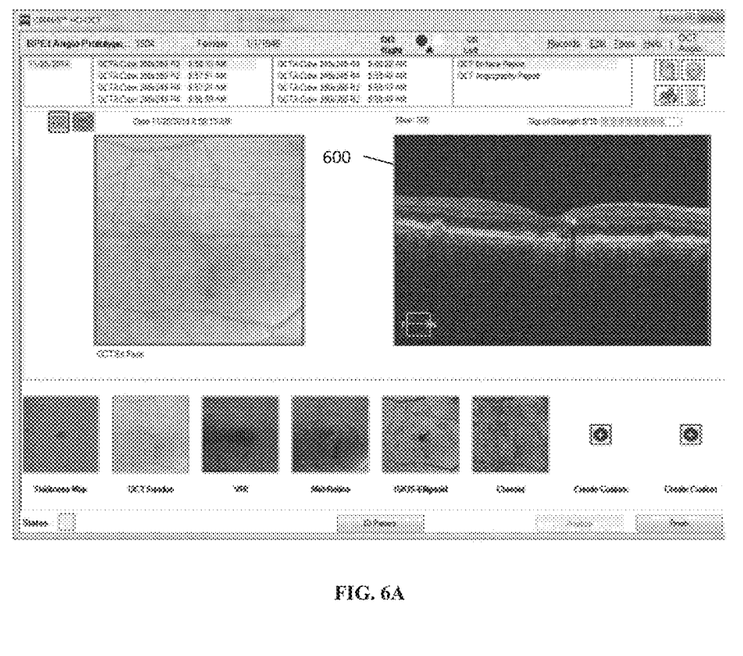
FIG. 6A shows display screens from a commercial OCT instrument used to record tissue tomogram highlighting a single B-scan within the volume.
Figure 6B:
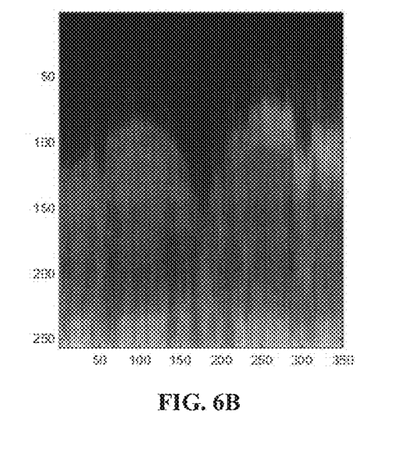
FIG. 6B shows a simulated autocorrelation B-scan resulting from the corresponding tissue reflectance profile.
Figure 6C:
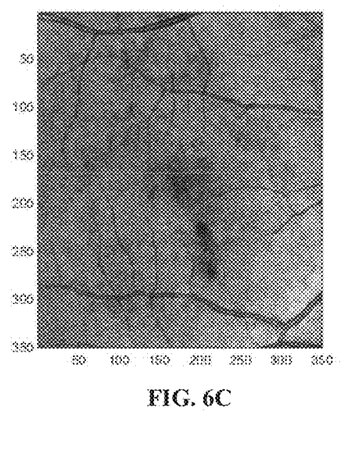
FIG. 6C is an en face projection of simulated autocorrelation data showing summed intensity over depth.
Figure 6D:
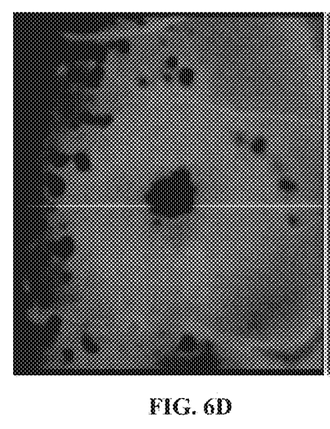
FIG. 6D shows en face projection of measured tissue thickness.
Figure 6E:
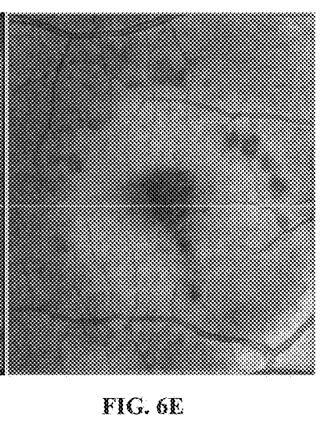
FIG. 6E shows an en face projection of summed reflectivity intensity over depth with an overlay projection that represents measured tissue depth.

FIGS. 6A-E illustrate the display of characteristics based on simulated data from a single high density volume recorded from one human eye. In particular, FIG. 6A shows a display screen from the commercial traditional OCT instrument (i.e., with a reference arm) used to record tissue tomogram highlighting a single B-scan 600 within the volume, which describes the reflectance profile of the tissue; FIG. 6B shows the simulated autocorrelation B-scan (i.e., without a reference arm) resulting from the corresponding tissue reflectance profile; FIG. 6C is an en face projection of simulated autocorrelation data showing summed intensity over the full depth, where low pixel value represents low tissue reflectivity; FIG. 6D shows an enface projection of the measured tissue thickness, where low pixel value represents low tissue thickness; and FIG. 6E shows the en face projection of summed reflectivity intensity over depth with an overlay projection that represents measured tissue depth in the same view. On a color display, overlaid images can be effectively presented without ambiguity, where the pixel brightness represents the summed reflectivity intensity and the hue represents the measured thickness of the tissue.

The self-referenced image reconstruction is the autocorrelation of scatter intensity in the axial direction. The vertical axis is the separation between any two scatters along the axial direction, and the intensity is the product of their reflected intensities. In the simulated data shown in FIGS. 6A-E, the image space is dominated by a structure with form strongly resembling the neurosensory retina. The dominant reflective layer in the healthy fundus is the retinal pigment epithelium (RPE), a thin layer deep to the retina. The primary tissue of interest, the neurosensory retina, is a very mildly scattering tissue consisting of several layers proximal to the RPE. Below the RPE are highly vascular networks called the choriocapillaris and choroid. Because the autocorrelation reports only the distance between scatterers and not the direction, the signal generated between the RPE and the interesting retina, are superimposed upon the signal generated between the RPE and the less interesting layers deep to it.

The RPE contains a large amount of melanin pigment—the same pigment responsible for giving human skin its brown color. The melanin of the eye strongly absorbs visible light, and is also absorptive in the near IR. Using illumination of shorter wavelength ranges (e.g., 700-800 nm rather than 800-900 nm) is beneficial for attenuating confusing signal originating from below the RPE. Blood rushing through these deep layers causes rapid phase fluctuations in the light scattered from these layers (see for example, Fingler, J., Zawadzki, R. J., Werner, J. S., Schwartz, D., and Fraser, S. E. (2009) "Volumetric microvascular imaging of human retina using optical coherence tomography with a novel motion contrast technique." Optics Express 17, 22190). Averaged over time, the contribution from deep layers will be reduced by phase washout. By measuring with a long integration time (e.g., time longer than 0.2 ms), or by combining multiple measurements separated in time, the measurement procedure can be adjusted to enhance this attenuation.

The easiest characteristic to measure and report from the recorded data is the summed scattering intensity. This can produce a high contrast en face image similar to a scanning laser ophthalmoscope. Additionally, the reconstructed B-scan can be segmented to determine the retinal thickness. If the RPE is not intact as a single, bright, reflecting surface within the bulk of the tissue (e.g., retina) to form the strongest optical interference, the image as a B-scan becomes more difficult to interpret by tissue structure. Because the nature of autocorrelation is still to describe the distance between scatters, it may still be possible to describe the thickness of the retina in this case. Note also that traditional OCT has more difficulty reporting retinal thickness when the RPE is severely disrupted. Even if no segmentation can be determined, the depth information contained in the autocorrelation may be able to determine subtle changes that would not be apparent from the summed intensity alone. If repeated measurements are acquired, such as from a low-cost home care device used on a daily or weekly basis, small changes in tissue thickness will cause changes in the interferogram and reconstruction which may trigger an alarm suggesting a visit to an ophthalmologist to get a full diagnostic scan and possible treatment.

Additional Reconstruction Techniques

We can model the tissue as a set of reflectors, one from each depth that can be resolved by the bandwidth of our system as follows:

$$f(x) = \text{sum}_i [A_i * \text{delta}(x - x_i)].$$

where $x_i$ is the distance to each resolved cell and $A_i$ is the amplitude of the net backscattering at that cell. At each wavenumber k, the wave arriving at the detector is a sum of complex sinusoids $$F(k) = \text{sum}_i [A_i \exp(j * k * x_i)]$$

This sum is the Fourier transform of the $A_i$ along the depth axis, so by measuring F(k) across the bandwidth we could theoretically recover f(x).

Since we only detect the magnitude of the resultant wave, though, we do not have the phase information needed to recover f(x). By the Wiener-Khintchine Theorem, the Fourier transform of $|F(k)|^2$ gives us the autocorrelation of f(x). The recovery of a signal from measurements of its spectral magnitude is a topic of general interest, though, and we may be able to use some of the work that has been done in this area.

A general approach for reconstruction is called alternating projections, in which constraints are iteratively applied in frequency domain and then in spatial domain. An early alternating-projection algorithm by Gerchberg and Saxton was devised for cases where both $|F(k)|$ and $|f(x)|$ are known, but can be adapted for our case by applying non-negativity and sparsity constraints in the spatial domain. For example, for the known signal f0:

```
N = 2^9; % Size of the subsampled A-scan
Sparsity=round(N*0.40); % number of pixels to be zeroed out at each iteration
NIter=7;
Sx=abs(fft(f0)); % sqrt of measured spectrum
% initialize with random phase
ph=2*pi*rand(N/2-1,1);
ph=[1;exp(i*2*pi*ph);0;exp(-i*2*pi*flipud(ph))];
fRec=real(ifft(sqrt(Sx).*ph));
PfR=fRec'*fRec; % power level to be maintained by normalization
% apply sparsity constraint
[~,iSort]=sort(fRec);
fRec(iSort(1:Sparsity))=0;
% apply nonnegativity constraint
fRec=max(0,fRec);
% shift energy toward middle
fRec=circshift(fRec,N/2-argmax(conv(fRec,ones(11,1))));
% normalize power
fRec=fRec*sqrt(PfR/(fRec'*fRec));
% restore measured magnitude but introduce phase from fRec
sRec=Sx.*exp(j*angle(fft(fRec)));
for Iter=2:NIter
    fRec(:,Iter)=real(ifft(sRec(:,Iter-1)));
    PfR=fRec(:,Iter)'*fRec(:,Iter);
    % apply sparsity constraint
    [~,iSort]=sort(fRec(:,Iter));
    fRec(iSort(1:Sparsity),Iter)=0;
    fRec(:,Iter)=max(0,fRec(:,Iter)); % nonnegativity constraint
    % shift energy toward middle
```

```
    fRec(:,Iter)=circshift(fRec(:,Iter),...
        N/2-argmax(conv(fRec(:,Iter),ones(11,1))));
    % normalize power
    fRec(:,Iter)=fRec(:,Iter)* ...
        sqrt(PfR/(fRec(:,Iter)'*fRec(:,Iter)));
    % restore measured magnitude but introduce phase from fRec
    sRec(:,Iter)=Sx.*exp(j*angle(fft(fRec(:,Iter))));
end
```

A shortcoming of this approach is that the non-negativity and sparsity constraints will be equally satisfied by the same data regardless of shift or flip. So, the location and orientation of the A-scans would need to be determined somehow. For evaluation purposes only, the data were aligned to the true data, a "cheat" useful only for determining whether the unaligned A-scans are being well reconstructed.

Figure 7A:
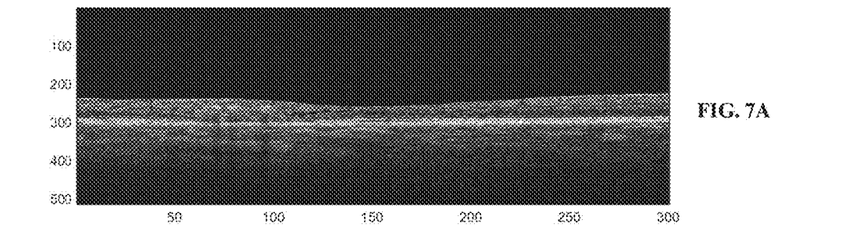
FIG. 7A shows a traditional B-scan collected with a reference arm used as source data for simulation and FIG. 7B shows a simulated reconstruction of the autocorrelation B-scan using non-negativity and 40% sparsity requirements at each iteration in spatial domain.
Figure 7B:
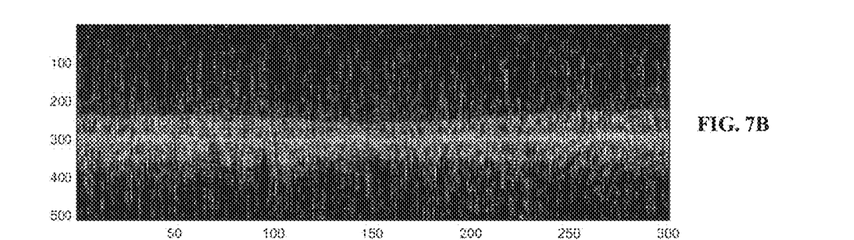

FIGS. 7A-B and FIGS. 8A-B illustrate examples of reconstruction using the above discussed approach. In particular, FIG. 7A shows a traditional B-scan collected with a reference arm used as source data for simulation and FIG. 7B shows a simulated reconstruction of the autocorrelation B-scan (i.e., collected without a reference arm) using non-negativity and 40% sparsity requirements at each iteration in spatial domain. The reconstructed A-scans were aligned to the original, for purposes of evaluating the quality of the reconstructions without solving the alignment ambiguity.

Figure 8A:
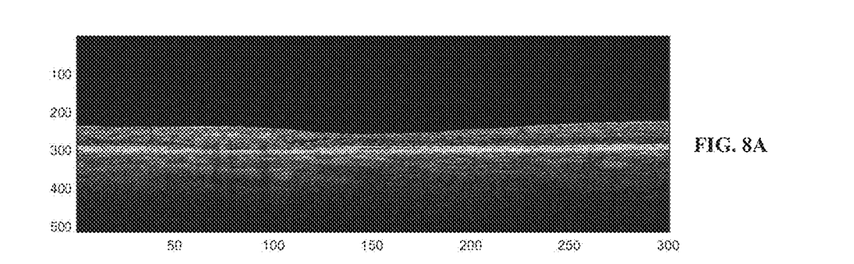
FIG. 8A shows a traditional B-scan collected with a reference arm used as source data for simulation and FIG. 8B shows the reconstruction of the autocorrelation B-scan after taking an average of five runs from different random starting points, using non-negativity and 40% sparsity requirements at each iteration in spatial domain.
Figure 8B:
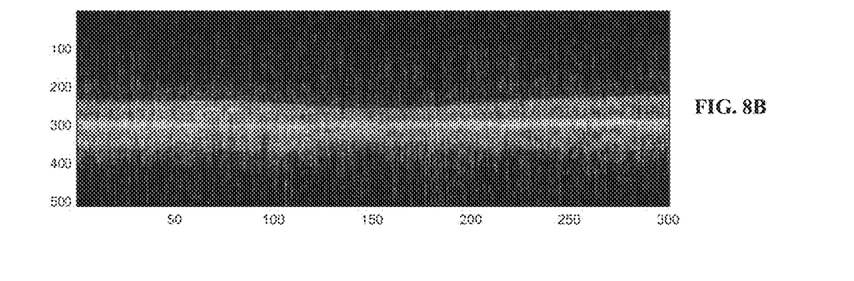

FIG. 8A shows a traditional B-scan collected with a reference arm used as source data for simulation and FIG. 8B shows the reconstruction of the autocorrelation B-scan (i.e., collected without a reference arm) after taking an average of five runs from different random starting points, using non-negativity and 40% sparsity requirements at each iteration in spatial domain. The reconstructed A-scans were aligned to the original, for purposes of evaluating the quality of the reconstructions without solving the alignment ambiguity.

Figure 9:
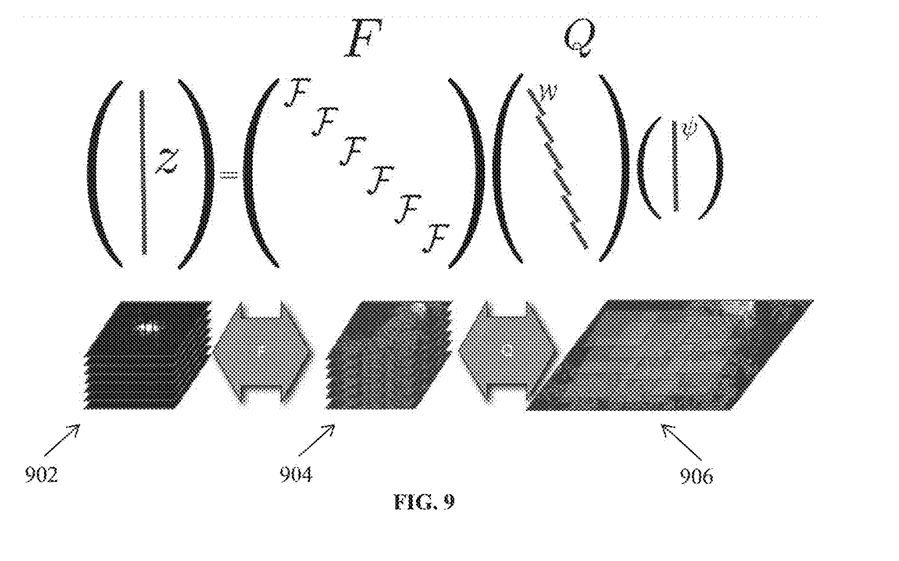
FIG. 9 shows a Ptychography example from X-ray diffraction imaging.

Instead of trying to reconstruct each A-scan independently, one can also try using multiple "looks" at each location. Ptychography is a method in which multiple overlapping images are acquired at each point, with each image giving a differently weighted combination of each location and its neighbors. The location of the overlapping scans is known and can possibly be inverted to give reconstructed data at each location. In some instances, spectral magnitude from the overlapping scans can be combined to estimate spectral phase. FIG. 9 shows a Ptychography example from X-ray diffraction imaging. Multiple images of diffraction pattern amplitude $|z_i|$ (indicated by reference numeral 902) are acquired at overlapping positions denoted by Q. F represents the separate Fourier transformation of each image. Reference numeral 904 represents the images after the Fourier transformation. ψ is the image to be reconstructed (indicated by reference numeral 906) (see for example, Yang, C., Qian, J., Schirotzek, A., Maia, F., Marchesini, S. (2011). "Iterative Algorithms for Ptychographic Phase Retrieval." Technical report LBNL-4598E).

As shown in the figure, the overlap is described by matrix Q. An iterative solution for each block in the image is $$\psi^{(J+1)} = Q(Q^*Q)^{-1}Q^* \mathcal{F}^* [Q\psi^{(J)} / +Q\psi^{(J)}|] \cdot | \mathcal{F}^* Q\psi^{(J)} |$$

where ψ is the image to be reconstructed, and F represents the separate Fourier transformation of each image (see for example, Eq. 33 in Yang, C., Qian, J., Schirotzek, A., Maia, F., Marchesini, S. (2011). "Iterative Algorithms for Ptychographic Phase Retrieval." Technical report LBNL-4598E). If Q represents the lateral scanning of a beam that spans several A-scans across the B-scan (a convolution), Q could be formulated as a Toeplitz matrix, which may give some computational advantages in the inversion of Q*Q by using Levinson-Durbin recursion. In any case, this matrix only needs to be inverted once for a given scanning pattern, and the result can be implemented as fixed coefficients for the system. This algorithm is guaranteed to converge to a stationary point, but may be slow; other algorithms may accelerate this convergence.

Data collected by the self-referenced device may be, on its own, in sufficient for good visualization or computer aided diagnosis. It may be advantageous to use known structural information from a full OCT scan to use as 'a prior knowledge' informing the algorithm. If the information is sufficiently oversampled in the lateral direction, one can additionally place a constraint that neighboring A-scans contain at least a lower bound amount of mutual information.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiment(s) of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. A method of analyzing a sample tissue using an interferometry system, said method comprising:
   illuminating the sample tissue with a beam of light using a spectrally broadband source;
   collecting a light signal scattered from the sample tissue at a detector, wherein the light signal travels along a single path between the sample tissue and the detector, said light signal resulting from optical interference between light scattered from multiple scatterers located at different depths in the sample tissue, wherein the light signal is dominated by light scattered from a dominant scatterer located within the bulk of the sample tissue;
   determining one or more characteristics of the sample tissue based on the collected light signal, said characteristics containing information about the distribution of depth separation between the multiple scatterers referenced to the dominant scatterer within the sample tissue; and
   displaying or storing the characteristics or a further analysis thereof.

2. The method as recited in claim 1, wherein the sample tissue is a human retina.

3. The method as recited in claim 2, wherein the one or more characteristics include retinal thickness.

4. The system as recited in claim 3, further comprising generating a fundus thickness map from the collected signal.

5. The method as recited in claim 2, wherein the scatterer located within the bulk of the sample tissue whose scattered light dominates the light signal is the retinal pigment epithelium (RPE).

6. The method as recited in claim 1, wherein the wavelength range of the spectrally broadband source is between 700-800 nm.

7. The method as recited in claim 1, wherein no separate beam path exists from the source to the detector to serve as a reference surface for the interference.

8. The method as recited in claim 1, wherein the spectrally broadband source is a multimode swept source.

9. The method as recited in claim 1, wherein the beam of light illuminating the sample tissue is a line beam.

10. The method as recited in claim 1, wherein the one or more characteristics include total reflectance of a tissue location.

11. The method as recited in claim 1, wherein the one or more characteristics include a total estimated depth of the tissue and/or an estimated depth of a tissue layer.

12. The method as recited in claim 1, further comprising processing the signal to reconstruct a spatial representation of a B-scan.

13. The method as recited in claim 1, wherein the illuminating and collecting steps are performed along separate spatial paths.

14. The method as recited in claim 1, further comprising using phase recovery to resolve ambiguity in the depth distribution of the multiple scatterers.

15. The method as recited in claim 1, wherein the collecting step has an integration time of more than 0.2 ms.

* * * * *

UNITED STATES PATENT AND TRADEMARK OFFICE
CERTIFICATE OF CORRECTION

PATENT NO. : 10,045,692 B2
APPLICATION NO. : 15/429084
DATED : August 14, 2018
INVENTOR(S) : Alexandre R. Tumlinson et al.

It is certified that error appears in the above-identified patent and that said Letters Patent is hereby corrected as shown below:

In the Specification

In Column 1, Line 60, delete "'autocorrelation noise." and insert -- 'autocorrelation noise'. --, therefor.

In Column 4, Line 24, delete "choriocapilaris," and insert -- choriocapillaris, --, therefor.

Signed and Sealed this
Eleventh Day of June, 2019

Andrei Iancu
*Director of the United States Patent and Trademark Office*